United States Patent [19]

Willemsens et al.

[11] Patent Number: 5,663,354
[45] Date of Patent: Sep. 2, 1997

[54] PROCESS FOR PREPARING ENANTIOMERICALLY PURE 6-[(4-CHLOROPHENYL) (1H-1,2,4-TRIAZOL-1-YL) METHYL]-1-METHYL-1H-BENZOTRIZOLE

[75] Inventors: Albert Louis Anna Willemsens, Beerse; Walter Louis Antoine Verstappen, Kontich; Alex Herman Copmans, Lille; Anna Maria Jozefa Vandendriessche, Oostmalle; Alfons Gaston Maria De Knaep, Turnhout, all of Belgium; Marc Gaston Venet, Le Mesnil Esnard, France

[73] Assignee: Janssen Pharmaceutica, N.V., Beerse, Belgium

[21] Appl. No.: 424,295

[22] PCT Filed: Nov. 2, 1993

[86] PCT No.: PCT/EP93/03066

§ 371 Date: Apr. 18, 1995

§ 102(e) Date: Apr. 18, 1995

[87] PCT Pub. No.: WO94/11364

PCT Pub. Date: May 26, 1994

[30] Foreign Application Priority Data

Nov. 10, 1992 [EP] European Pat. Off. ............. 92203443

[51] Int. Cl.[6] .................................... C07D 403/06
[52] U.S. Cl. .................................... 548/257
[58] Field of Search .............................. 548/257

[56] References Cited

FOREIGN PATENT DOCUMENTS 0293978 12/1988 European Pat. Off. .
0371559 6/1990 European Pat. Off. .

OTHER PUBLICATIONS

Wouters et al., "Comparative Effects of the Aromatase Inhibitor R76713 and of its Enantiomers R83839 and R83842 on Steroid Biosynthesis in Vitro and in Vivo", *J. Steroid Biochem. Molec. Biol.*, vol. 37, No. 6, pp. 1049–1054, 1990.

Vanden Bossche et al., "R 76713 and Enentiomers: Selective, Nonsteroidal Inhibitors of the Cytochrome P450–Dependent Oestrogen Synthesis", *Biochemical Pharmacology*, vol. 40, No. 8, pp. 1797–1718, 1990.

*Primary Examiner*—Patricia L. Morris
*Attorney, Agent, or Firm*—Charles J. Metz

[57] ABSTRACT

A process for preparing (+)-6-[(4-chlorophenyl)(1H-1,2,4-triazol-1-yl)methyl]-1-methyl-1H-benzotriazole comprising the resolution of (±)-6-[(4-chlorophenyl)-hydrazinomethyl)-1-methyl-1H-benzotriazole and converting the appropriate enantiomerically pure hydrazine intermediate into (+)-6-[(4-chlorophenyl)(1 H-1,2,4-triazol-1-yl)methyl]-1-methyl-1H-benzotriazole.

4 Claims, No Drawings

PROCESS FOR PREPARING ENANTIOMERICALLY PURE 6-[(4-CHLOROPHENYL) (1H-1,2,4-TRIAZOL-1-YL) METHYL]-1-METHYL-1H-BENZOTRIZOLE

CROSS-REFERENCE TO RELATED APPLICATIONS

This application is based upon PCT application Ser. No. PCT/EP 93/03066, filed Nov. 2, 1993, published as WO94/11364, May 26, 1994, which claims priority from European Application Ser. No. 92.203.443.4, filed on Nov. 10, 1992.

BACKGROUND OF THE INVENTION

In U.S. Pat. No. 4,943,574 there are described 1H-azol-1-ylmethyl substituted benzotriazole derivatives which are potent aromatase inhibitors. These compounds are useful in treating estrogen hormone dependent disorders in mammals. 6-[(4-chlorophenyl) (1H-1,2,4-triazol-1-yl)methyl]-1-methyl]1H-benzotriazole in particular is a highly potent and selective inhibitor of the human aromatase. Most of its activity and selectivity, however, originates from its dextrorotatory (S)-enantiomer. Resolution of the racemic benzotriazole compound by selective crystallization of its diastereomeric salts proved impractical.

The present invention is concerned with a process for separating the enantiomers of a hydrazinc intermediate. Said separation is obtained by the selective crystallization of the diastereomeric salts of said intermediate with chiral acids or by chromatographically separating diastereomeric covalent compounds derived from said hydrazine derivative and a chiral acid. The enantiomerically pure intermediate then is further converted into the desired dextrorotatory (S)-benzotriazole end product.

DESCRIPTION OF THE INVENTION

The present invention is concerned with a process of preparing enantiomerically pure 6-[(4-chlorophenyl)(1H-1,2,4-triazol-1-yl)methyl]1-methyl-1H-benzotriazole having the formula

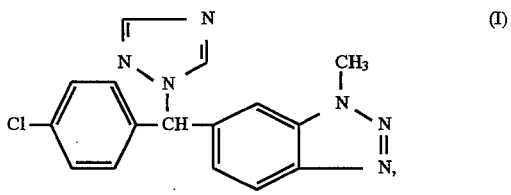

and the pharmaceutically acceptable acid addition salt forms thereof.

In the foregoing definitions and hereinafter the term 'enantiomerically pure' concerns compounds having an enantiomeric excess of at least 80% (i.e. minimum 90% of one enantiomer and maximum 10% of the other enantiomer) up to an enantiomeric excess of 100% (i.e. 100% of one enantiomer and none of the other), in particular compounds having an enantiomeric excess of 90% up to 100%, more in particular having an enantiomeric excess of 94% up to 100% and most in particular having an enantiomeric excess of 97% up to 100%. The term 'enantiomerically enriched' concerns compounds having an enantiomeric excess of up to 80%. The terms 'diastereomerically pure' and 'diastereomerically enriched' as used hereinafter should be understood in a similar way, but then having regard to the diastereomeric excess of the mixture in question.

The compound of formula (I) has weak basic properties and, consequently, it may be converted into a therapeutically active non-toxic acid addition salt form by treatment with an appropriate acid. Conversely the salt form can be converted by treatment with alkali into the free base form. The term pharmaceutically acceptable acid addition salts also comprises the solvates which the compound of formula (I) may form. Examples of such solvates are hydrates and alcoholates.

As used hereinafter halo represents fluoro, chloro, bromo and iodo, in particular bromo; $C_{1-4}$alkyl defines straight and branch chained saturated hydrocarbon radicals having from 1 to 4 carbon atoms such as, for example, methyl, ethyl, propyl, 1-methylethyl, butyl, 1,1-dimethylethyl, 1-methylpropyl and 2-methylpropyl; $C_{1-6}$alkyl defines $C_{1-4}$alkyl radicals as defined hereinabove and the higher homologs thereof having 5 or 6 carbon atoms, e.g. pentyl or hexyl; $C_{5-7}$cycloalkyl is generic to cyclopentyl, cyclohexyl and cycloheptyl.

Each Aryl is phenyl optionally substituted with 1 or 2 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino and $C_{1-6}$alkylcarbonyl.

Hereinafter, the notation (±) denotes the racemic mixtures, whereas (A) denotes an enantiomerically or diastereomerically enriched or pure fraction of the intermediate which yields upon further reaction the desired dextrorotatory (S)-enantiomer of formula (I), which may be represented by the notation (S)-(+)-(I). The reactions and claims hereinafter specifically describe the preparation of compounds (S)-(+)-(I). Obviously, the same reactions when conducted with the mirror images of the chiral reagents used in the following description will yield the compound (R)-(−)-(I). These reactions, although not explicitly disclosed, are also intended to be included within the present scope and claims.

In particular, the present invention concerns a process of preparing the compound of formula (I) as defined hereinabove, characterized by a) resolving the racemic mixture of the intermediate of formula (II)

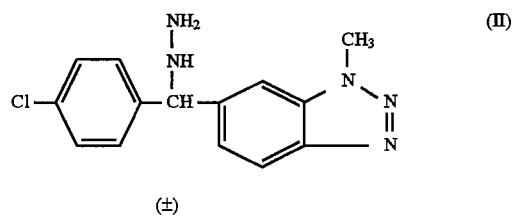

i) by converting said racemic mixture of intermediate (II) into a mixture of diastereomeric salts with one of the enantiomers of a chiral acid in a reaction-inert solvent such as, for example, an alcohol e.g. methanol, ethanol, 2-propanol, an ester, e.g. ethyl acetate or a mixture of such solvents, and collecting the desired diastereomeric salt of formula (A)(III) either from the precipitate or from the mother liquor,

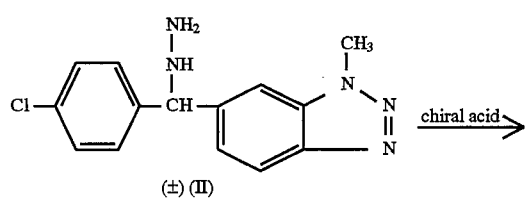

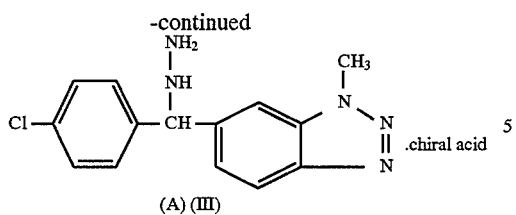

(A) (III)

ii) or, by converting said racemic mixture of intermediate (II) into a mixture of diastereomeric covalent compounds of formula (IV) with one of the enantiomers of a chiral acid of formula (V) or a reactive derivative thereof wherein $R^1$ represents hydrogen or $C_{1-4}$alkyl and Aryl represents phenyl optionally substituted with 1 or 2 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino and $C_{1-6}$alkylcarbonyl, following an-known procedures, separating the diastereomers of formula (IV) e.g. by column chromatography or crystallization and collecting the desired diastereomeric compound of formula (A)(IV);

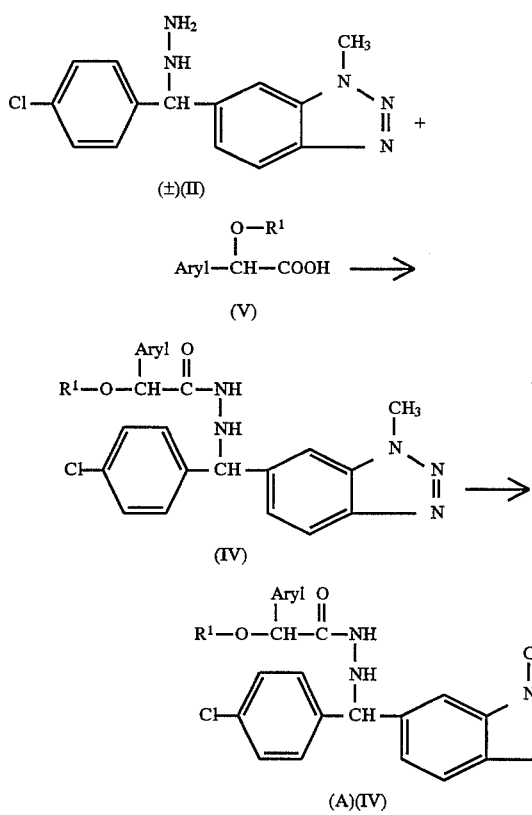

b) and, converting the salt of formula (A)(III) or the compound of formula (A)(IV) into an enantiomerically pure form of compound (S)-(+)-(I) by cyclization with methanimidamide, triazine, formamide or an acid addition salt thereof, in a reaction inert solvent such as, for example, water, an alcohol, e.g. methanol, ethanol, 2-propanol, a halogenated hydrocarbon, e.g. dichloromethane, trichloromethane, chlorobenzene or a mixture of such solvents.

(A)(III) or (A)(IV) $\xrightarrow{\text{cyclization}}$

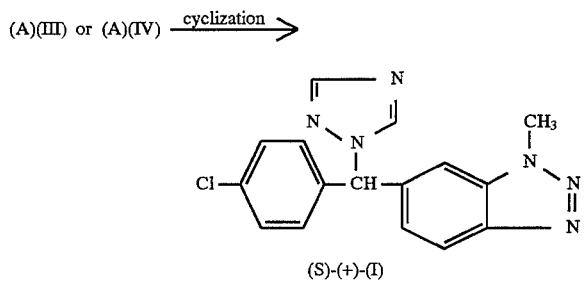

(S)-(+)-(I)

The acid used in reaction step a) i) is added to the solution of the hydrazine compound of formula (II) either as a solid or dissolved in a small amount of solvent. Stirring and, if necessary, heating is continued until a clear solution is obtained. The solution then is cooled slowly to ambient temperature or slightly lower, preferably to a temperature between 0° and 25° C. This slow cooling can effectively be accomplished by turning off the heat source and optionally removing the heat source thus facilitating heat exchange with the environment. In case a very large volume to area ratio of the reaction vessel would delay spontaneous cooling too long, the cooling may be accelerated by any cooling means known in the art.

Upon cooling, one diastereomeric salt form of formula (III) crystallizes whereas the other diastereomeric salt form and/or the unreacted enantiomer of formula (II) remain in solution.

When the desired isomer is contained in the crystallized fraction, said isomer can conveniently be collected by filtration. In order to promote the crystallization it may be advantageous to add an amount of water to the solution. A preferred manner of promoting crystallization, however, comprises seeding the solution with some crystals of (A)-(III) obtained in a separate run. The precipitated crystals may optionally be allowed to digest before collection by filtration. Crystal digestion may be accomplished by continuing to stir the mixture and may proceed for any moment of time up to about a day, preferably for about 0 to 4 hours, and in some instances may be left out altogether. The precipitate is filtered off, and may be washed with additional solvent, preferably a small amount of cold solvent. The product is dried by conventional means such as under vacuum, optionally at an enhanced temperature. After filtering off and drying, the crystals may optionally be purified by recrystallization from an appropriate solvent such as water, an alcohol, e.g. methanol, ethanol, 1-propanol, 2-propanol, preferably ethanol or 2-propanol, or a mixture of such solvents. Said recrystallization may be useful for further increasing the diastereomeric excess of the crystalline diastereomeric salt.

When the desired isomer is contained within the mother liquor, said isomer can be isolated following techniques known in the art, said techniques usually comprise evaporating the solvent, subsequently crystallizing the residue and optionally recrystallizing and drying the obtained crystals.

Optionally, the racemic mixture of intermediate of formula (±)-(II) may be recovered by racemization of the undesired isomer of formula (III) or of formula (IV). Said racemization, may result from reacting the undesired enantiomer of formula (III) in a reaction-inert solvent, such as an alcohol, e.g. methanol, ethanol, 1-propanol, 2-propanol and the like, in the presence of a base such as sodium hydroxide, potassium hydroxide, sodium hydride and the like. The racemization may also be carried out by first transforming the undesired isomer of formula (III) or (IV) into a derivative more prone for racemization, and subjecting said derivative to the above mentioned racemization conditions.

The preferred chiral acids to be used in reaction step a) i) are (R)-(−)-α-hydroxy benzeneacetic acid, (+)-4-(2-chlorophenyl)-dihydro-2-hydroxy-5,5-dimethyl-4H-1,3,2-dioxaphosphorin-2-oxide or (S)-(−)-α-[[(phenylamino)carbonyl]oxy]propanoic acid. The most preferred chiral acid used in reaction step a) i) is (R)-(−)-α-hydroxybenzeneacetic acid. The main advantages of said chiral acid are the higher enantiomeric excess that is obtained when compared to the other acids and its commercial availability.

Moreover, when using said most preferred chiral acid, the desired (S)-isomer can be collected directly from the precipitate. The use of (S)-(−)-α[[(phenylamino)carbonyl]oxy] propanoic acid results in an enrichment of the desired compound in the mother liquor.

The preferred chiral acid used in reaction step a) ii) is (R)-(−)-α-methoxybenzeneacetic acid.

When using (R)-(−)-α-hydroxybenzeneacetic acid, as a resolving agent, in reaction step a) i), the crystallization step should be conducted in the presence of a small amount of water. A hydrated salt form of formula (A)(VI)

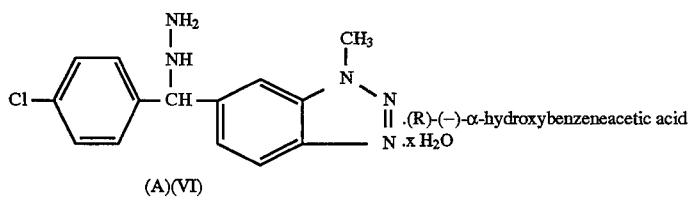

wherein x is 1, 2 or a number between 1 and 2, is then obtained.

Further, when using (R)-(−)-α-hydroxybenzeneacetic acid in reaction step a) i), the ratio of the reagents was found to influence the yield of the reaction and the enantiomeric excess of the obtained compound. Preferably, for 1 mole of the racemic mixture of starting product of formula (II), 0.5 to 10 liter of alcohol, 0.1 to 1 liter of water and 0.5 to 1 mole of the chiral acid are used. The most preferred mode of conducting the described process involves 1 mole of the starting compound of formula (II), about 0.8 liter of alcohol, about 0.35 liter of water and about 0.55 mole of the chiral acid.

Apart from the direct cyclization reaction as described in reaction step b) hereinabove, the compound of formula (S)-(+)-(I) can also be obtained by a procedure which allows the chiral acid, incorporated in the salt of formula (A)(III) or in the diastereomeric compound of formula (A)(IV), to be recovered from the reaction mixture. When the starting product in reaction step b) is the salt of formula (A)(III), said procedure is characterized by first (i) converting the salt form of formula (A)(III) into the free base by treatment with a base dissolved in water, optionally in admixture with an immiscible organic solvent, thus yielding an intermediate of formula (A)(VII), while the chiral acid may be recovered from the aqueous layer following art-known procedures,

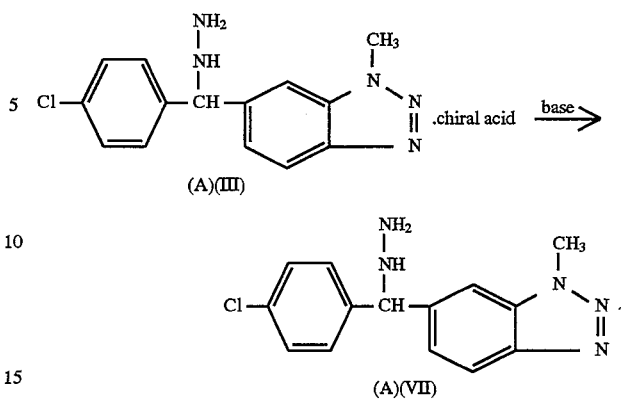

(ii) converting the base form of formula (A)(VII) into a salt form of formula (A)(VIII) by treatment with an acid, such as, for example, hydrochloric acid, sulfuric acid and the like, in a reaction-inert solvent, such as, for example, water, an alcohol, e.g. methanol, ethanol, 2-propanol or a mixture of such solvents,

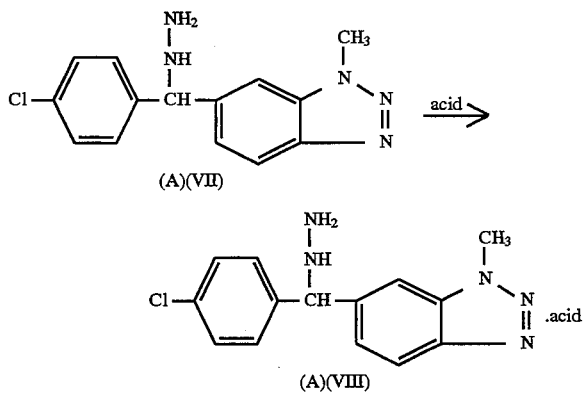

(iii) and subsequently cyclizing the intermediate of formula (A)(VIII) as described for intermediate (A)(III) hereinabove, thus yielding the desired compound of formula (S)-(+)-(I) in an enantiomerically pure form.

When on the other hand the compound of formula (I) is to be obtained from the diastereomeric compound of formula (A)(IV), a procedure which allows the chiral acid to be recovered from the reaction mixture is the following:

(i) reacting an intermediate of formula (A)(IV) in a solvent such as an aqueous alcohol, e.g. methanol, ethanol, 2-propanol, in the presence of a dilute acid such as, for example, hydrochloric acid, sulfuric acid and the like, preferably at an elevated temperature, e.g. the reflux temperature and subsequently adding an appropriate base such as, for example, ammonium hydroxide, thus yielding an intermediate of formula (A)(VII) while the chiral acid may be recovered from the aqueous layer following art-known procedures,

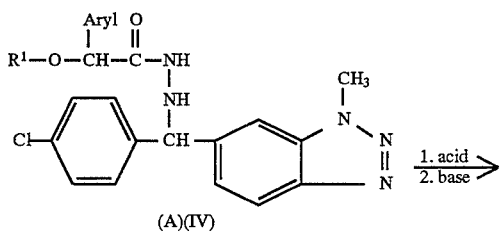

(A)(IV)

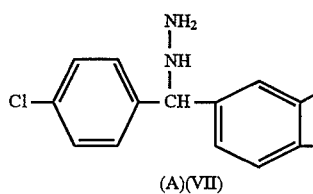

(A)(VII)

(ii) converting the base form of formula (A)(VII) into a salt form of formula (A)(VIII) by treatment with an acid, such as, for example, hydrochloric acid, sulfuric acid and the like, in a reaction-inert solvent, such as, for example, water, an alcohol, e.g. methanol, ethanol, 2-propanol or a mixture of such solvents, as described hereinabove, (iii) and cyclizing the intermediate (A)(VIII) to a compound of formula (S)-(+)-(I) as described hereinabove.

In order to improve the stability of the hydrazine intermediate of formula (A)(VII), said intermediate can advantageously be converted into a carbonyl derivative thereof, which then is further cyclized into the compound of formula (S)-(+)-(I). The corresponding procedure is characterized by first (i) reacting an intermediate of formula (A)(VII) with a reagent of formula R—C(=O)X, wherein R represents hydrogen, $C_{1-6}$alkyl, $C_{1-4}$alkyloxy, ($C_{1-4}$alkyloxy)(Aryl)-methyl, $C_{5-7}$cycloalkyl, Aryl$C_{1-4}$alkyl or Aryl, and X is RC(=O)O—, halo or $OR^2$, $R^2$ being hydrogen, $C_{1-4}$alkyl or Aryl, optionally in a reaction-inert solvent such as a halogenated hydrocarbon, for example, dichloromethane, trichloromethane, chlorobenzene and the like, and optionally in the presence of a base such as, for example N,N-diethylethanamine, N,N-di(1-methylethyl)-ethanamine, 4-ethylmorpholine, pyridine and the like, thus yielding an intermediate of formula (A)(IX).

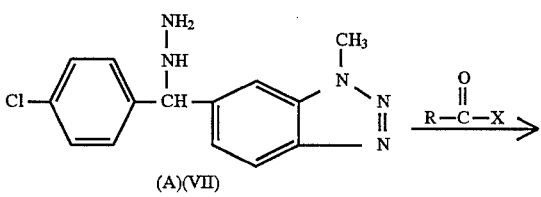

(A)(VII)

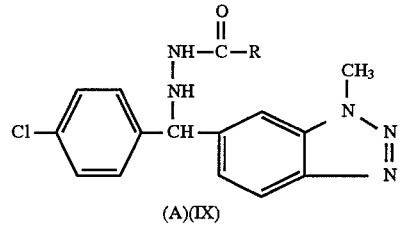

(A)(IX)

(ii) and cyclizing the intermediate of formula (A)(IX) as described for intermediate (A)(III) hereinabove, thus yielding a compound of formula (S)-(+)-(I).

The racemic mixture of starting product of formula (II) used in reaction step a) can be obtained by reacting an intermediate of formula (X) wherein W represents a reactive leaving group such as, for example, halo, e.g. chloro, bromo or iodo, or a sulfonyloxy group, e.g. methanesulfonyloxy, trifluoromethanestalfonyloxy, benzenesulfonyloxy, 4-methylbenzenesulfonyloxy, 2-naphthalenesulfonyloxy and the like, with hydrazine or an acid addition salt thereof in a reaction-inert solvent in the presence of a base.

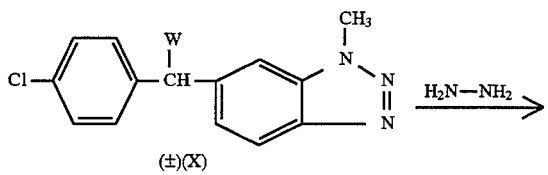

(±)(X)

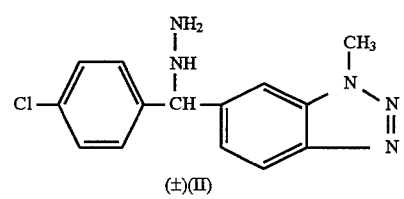

(±)(II)

The intermediate of formula (II) may also be obtained by
(i) reacting an intermediate of formula (X) with a reagent of formula $H_2N$—NH—COR (XI), wherein R represents hydrogen, $C_{1-6}$alkyl, $C_{1-4}$alkyloxy, ($C_{1-4}$alkyloxy)-(Aryl)methyl, $C_{5-7}$cycloalkyl, Aryl$C_{1-4}$alkyl or Aryl, in a reaction-inert solvent in the presence of a base,

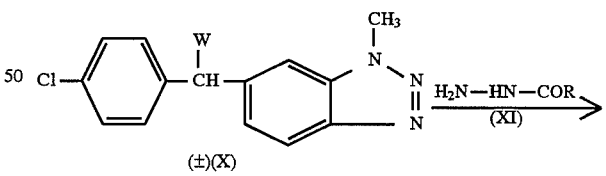

(±)(X)

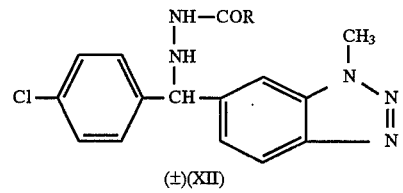

(±)(XII)

(ii) hydrolyzing the compound of formula (XII) in a solvent such as, for example, water, an alcohol, e.g.

methanol, ethanol, 2-propanol, or a mixture of such solvents, in the presence of a dilute acid such as, for example, hydrochloric acid, sulfuric acid and the like, preferably at an elevated temperature, e.g. the reflux temperature, thus yielding a salt of formula (XIII),

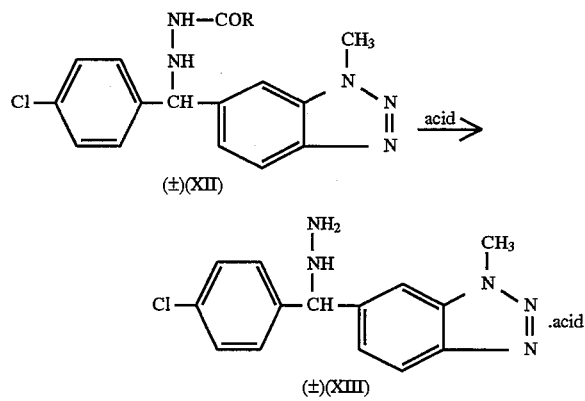

(iii) converting the salt form of formula (XIII) into the free base form (±)-(II) by treatment with a base in water, optionally in admixture with an organic solvent.

Reaction-inert solvents for the N-alkylations involving the intermediate of formula (X) described above are, for example, aromatic hydrocarbons, e.g. benzene, methylbenzene, dimethylbenzene, halogenated hydrocarbons, e.g. dichloromethane, trichloromethane, chlorobenzene, dipolar aprotic solvents, e.g. N,N-dimethylformamide, N,N-dimethylacetamide, dimethylsulfoxide, acetonitrile and the like. Appropriate bases to be used in said N-alkylations are, for example, N,N-diethylethanamine, N-(1-methylethyl)-2-propanamine, N,N-di(1-methylethyl)ethanamine and the like.

Stirring and somewhat elevated temperatures may enhance the rate of the reaction. Additionally, it may be advantageous to conduct the described reaction under an inert atmosphere such as, for example, oxygen-free argon or nitrogen gas.

Further, the intermediate of formula (II) may also be prepared by a procedure characterized by (i) reacting a carbonyl compound of formula (XIV) with an intermediate of formula (XI), in a reaction-inert solvent, thus yielding a hydrazone of formula (XV),

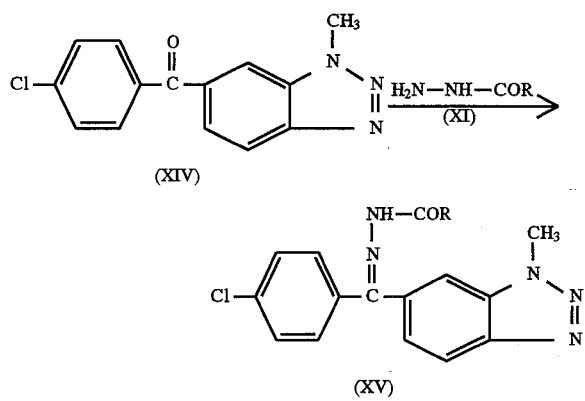

(ii) reducing the hydrazone of formula (XV) with an appropriate reducing agent in a reaction-inert solvent,

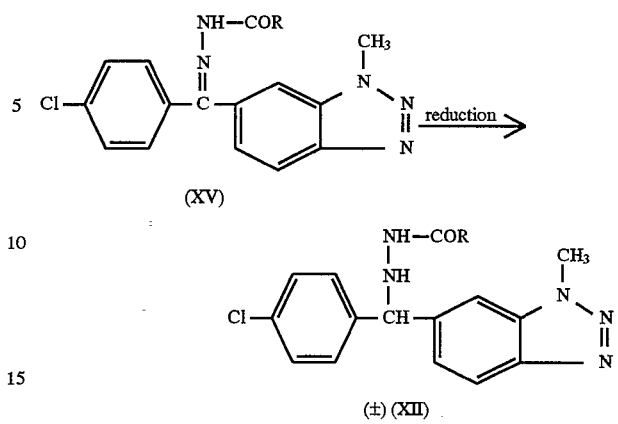

(iii) hydrolyzing the intermediate (XII) in the presence of a dilute acid and converting the thus obtained salt of formula (XIII) into the free base of formula (II) with alkali as described hereinabove.

Finally, the intermediate of formula (II) may also be obtained by (i) reacting a carbonyl compound of formula (XIV) with hydrazine, optionally in a reaction-inert solvent, yielding a hydrazone of formula (XVI),

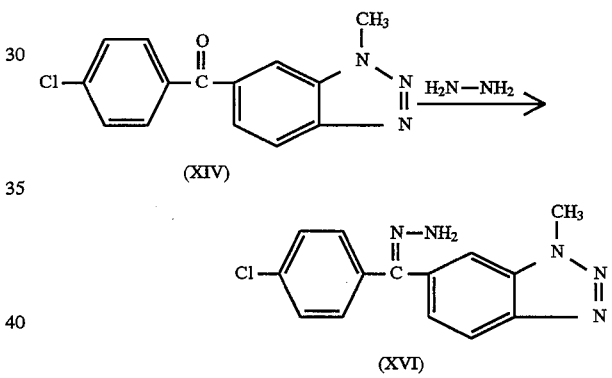

(ii) reducing the hydrazone of formula (XVI) with an appropriate reducing agent in a reaction-inert solvent.

In the reactions involving the carbonyl compound of formula (XIV) described hereinabove, an appropriate reaction-inert solvent is, for example, acetic acid or an alcohol, e.g. methanol, ethanol, 2-propanol and the like. The reduction of the hydrazone compounds of formula (XV) and (XVI) may be conducted using reducing agents such as borohydrides, aluminium hydrides, complex borohydrides, e.g. sodium borohydride, complex aluminium hydrides, e.g. lithium aluminium hydride, or by way of reaction under hydrogen atmosphere, optionally at an increased temperature and/or pressure, in the presence of an appropriate catalyst such as palladium-on-charcoal, platinum-on-charcoal and the like. Said reduction reaction is conducted in a reaction inert solvent such as an ether, for example, 1,1'-oxybisethane, 2,2'-oxybispropane, tetrahydrofuran and the like, optionally in the presence of an acid such as hydrochloric acid, sulfuric acid, acetic acid and the like.

According to a preferred embodiment of the process of the present invention, the free base of formula (II) where it is obtained from hydrolyzing the salt form of formula (XIII), is not isolated from the reaction mixture, but is converted in situ into the diastereomeric salt of formula (A)(III).

According to a further preferred embodiment of the process of the present invention, the free base form of formula (A)(VII) where it is obtained from the intermediate of formula (A)(III), is not isolated from the organic layer but is converted in situ into the salt form of formula (A)(VIII) by addition of an acid such as, for example, hydrochloric acid, sulfuric acid and the like.

These one pot approaches to the reaction steps described above exclude a number of manipulations and result in an increased yield.

The above described process per se for preparing a compound of formula (I) by converting a hydrazine into a triazole compound of formula (I), using an appropriate cyclizing agent, is new and is meant to be comprised within the present invention.

The intermediates of formula

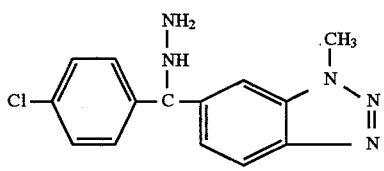

and

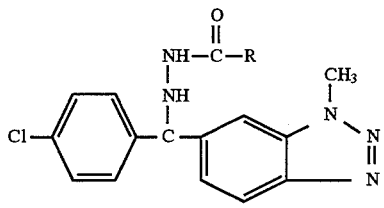

wherein R is hydrogen, $C_{1-6}$alkyl, $C_{1-4}$alkyloxy, $(C_{1-4}alkyloxy)(Aryl)methyl$, $C_{5-7}$cycloalkyl, $ArylC_{1-4}$alkyl or Aryl; the racemic mixture, the enantiomerically pure forms and the acid addition salts thereof, are deemed novel and are also meant to be comprised within the present invention.

The following examples serve to further illustrate the present invention.

EXPERIMENTAL PART

Example 1 a) A mixture of 669 g of 6-[bromo(4-chlorophenyl)methyl]-1-methyl-1H-benzotriazole monohydrobromide, 177 g of acetylhydrazide, 470 ml of N,N-diethylethanamine and 3.1 l methylbenzene was stirred for 4 hours at 60° C. under a nitrogen atmosphere. After the reaction mixture was cooled to 5° C., the precipitate was filtered off, washed with methylbenzene and stirred in 2.7 l water for 60 min. The product was filtered off, washed with water and dried in vacuo, yielding 445 g (87%) of (±)-2-[(4-chlorophenyl)(1-methyl-1H-benzotriazol-6-yl)methyl]hydrazide acetic acid (interm. 1-a).

b) A mixture of 445 g of intermediate 1-a, 450 ml of hydrochloric acid, 830 ml of water and 1350 ml of ethanol was stirred for 2 hours at reflux temperature. After stirring overnight at room temperature, the reaction mixture was cooled and stirred for 4 hours on ice-bath. The product was filtered off, washed with ethanol, and dried in vacuo, yielding 324.9 g (74%) of (±)-6-[(4-chlorophenyl)hydrazinomethyl]-1-methyl-1H-benzotriazole monohydrochloride (interm. 2-a).

c) To a mixture of 200 g of intermediate 2-a and 479 ml of ethanol at 23° C. was added a solution of 23.94 g of sodium hydroxide in 180 ml of water. After stirring for 10 min. there were added 50.2 g of (−)-(R) α-hydroxybenzeneacetic acid. The whole was stirred for 30 min. at 60° C. and the product was crystallized by adding some product crystals obtained in a previous low-scale set-up. Then the whole was stirred for 2 hours at 50° C. and overnight at room temperature. The reaction mixture was cooled (temp. 14° C.) and stirred for 1 hour. The product was filtered off, washed with ethanol and dried in vacuo, yielding 118.8 g (87%) of (−)-6-[(4-chlorophenyl)-hydrazinomethyl]-1-methyl-1H-benzotriazole (R)-α-hydroxybenzeneacetate (1:1) monohydrate (interm. 3-a); diastereomeric excess: 92.6%.

d) The mother liquor was acidified with 34 ml of hydrochloric acid (10N) and stirred for 90 min. at room temperature. The precipitate was filtered off, washed with ethanol and dried in vacuo, yielding 83.1 g (85%) of (−)-6-[(4-chlorophenyl)hydrazinomethyl]-1-methyl-1H-benzotriazole monohydrochloride (interm. 2-b); enantiomeric excess: 72%.

e) To a suspension of 8.1 g of intermediate 2-b in 60 ml of dichloromethane was added a solution of 1 g sodium hydroxide in 15 ml of water. The whole was stirred for 15 min., then the organic layer was separated and evaporated. The residue and 1.4 g of potassium hydroxide were refluxed in 50 ml ethanol for 3 hours, yielding (−)-6-[(4-chlorophenyl)hydrazinomethyl]-1methyl-1H-benzotriazole (interm. 2-c); enantiomeric excess: 20%.

f) To a mixture of 110 g of intermediate 3-a and 525 ml dichloromethane was added 8.4 g of sodium hydroxide in 84 ml water. The reaction mixture was stirred for 15 min. at room temperature. Then the organic layer was separated, dried and filtered. To the filtrate, there was added 60 ml of 2-propanol saturated with hydrochloric acid (3.5N) and the reaction mixture was stirred for 60 min. The precipitate was filtered off and dried, yielding 61.5 g (90%) of (+)-6-[(4-chlorophenyl)hydrazinomethyl]-1-methyl-1H-benzotriazole monohydrochloride (interm. 4-a); enantiomeric excess: 92.6%.

g) A mixture of 5 g of intermediate 4-a, 4.8 g of methanimidamide monoacetate and 15 ml of methanol was stirred for 1.5 hours at reflux temperature. After cooling to room temperature, the reaction mixture crystallized and there were added 30 ml of water. After stirring for 1 hour the precipitate was filtered off, washed with water and dried in vacuo at 50° C. The product was diluted with 11.8 ml of 2-propanol and the whole was treated with active charcoal for 15 min. at reflux temperature. The charcoal was filtered off while hot and washed with 2-propanol. The product was crystallized, filtered off and dried in vacuo at 50° C., yielding 3.3 g (66.0%) of (+)-6-[(4-chlorophenyl)-(1H-1,2,4-triazol-1-yl)methyl]-1-methyl-1H-benzotriazole (comp. 1-a); mp. 130°-135° C.; $[\alpha]_D^{20} = +8.0°$ (conc.=10% in $CH_3OH$); enantiomeric excess: 98.4%.

Example 2 a) To a stirred mixture of 1 l of hydrazine monohydrate and 0.5 l of acetonitrile was added dropwise and under nitrogen atmosphere a solution of 880 g of 6-[bromo (4-chlorophenyl)methyl]-1-methyl-1H-benzotriazole monohydrobromide in 1.7 l acetonitrile. After stirring for 16 hours at room temperature, the reaction mixture was poured in 6 l water and extracted with 1.1 l dichloromethane. The combined organic layers were dried and acidified with 600 ml of 2-propanol saturated with hydrochloric acid (3.5N). Then, the reaction mixture was stirred for 16 hours at 23° C. under a nitrogen atmosphere. The precipitate was filtered off, washed with 200 ml dichloromethane and dried in vacuo at 50° C., yielding 515.6 g (74%) of (±)-6-[(4-chlorophenyl)hydrazinomethyl]-1-methyl-1H-benzotriazole monohydrochloride (interm. 2-d).

b) To a suspension of 97.5 g of intermediate 2-d in 450 ml dichloromethane was added a solution of 12 g of sodium hydroxide in 250 ml of water. The whole was stirred for 45 minutes at 23° C. The organic layer was separated, dried, filtered and evaporated. The residue was mixed with 50 ml of methylbenzene and the whole was evaporated again. The residue was dissolved in 1.32 l of ethanol, heated to 55°-60° C. and 45.9 g of (−)-(R)-α-hydroxybenzeneacefic acid was added. Then, there were added 10.8 ml of water and the whole was stirred for 18 hours at 23° C. under a nitrogen atmosphere. The product was filtered off and dried at 50° C., yielding 52 g (73%) of (−)-6-[(4-chlorophenyl)hydrazinomethyl]-1-methyl-1H-benzotriazole (R)-α-hydroxybenzeneacetate (1:1) dihydrate (interm. 3-b) $[\alpha]_D^{20}$=−25.3° (conc.=1% in DMF); diastereomeric excess: 83.4%.

c) 20 g of intermediate 3-b was recrystallized from 200 ml of ethanol. The whole was stirred for 16 hours at 23° C. and the product was filtered off, yielding 15.8 g (78.9%) of (−)-6-[(4-chlorophenyl)hydrazinomethyl]-1-methyl-1H-benzotriazole (R)-α-hydroxybenzeneacetate (1:1) monohydrate; mp. 137.9° C.; diastereomeric excess: 98.2%; $[\alpha]_D^{20}$=−17.92° (conc.=1% in CH$_3$OH) (interm. 3-c).

d) To a mixture of 11 g of intermediate 3-c and 40 ml of dichloromethane was added a solution of 1 g of sodium hydroxide in 20 ml of water. After stirring for 10 min. at at room temperature, the organic layer was separated, dried and filtered. Then there were added 7.15 ml of 2-propanol saturated with hydrochloric acid. (3.5N). The whole was stirred for 1 hour and the product was filtered off and dried in vacuo at 45° C., yielding 6.9 g (85%) of (+)-6-[(4-chlorophenyl)hydrazinomethyl]-1-methyl-1H-benzotriazole monohydrochloride (interm. 4-b); enantiomeric excess: 99% e) 6.9 g of intermediate 4-b was recrystallized from 30 ml 2-propanol yielding 5.1 g (74%) of (+)-6-[(4-chlorophenyl)hydrazinomethyl]-1-methyl-1H-benzotriazole monohydrochloride (interm. 4-c); mp. 250.6° C.; $[\alpha]_D^{20}$=+26.23° (conc.=1% in CH$_3$OH).

f) To a mixture of 11 g of intermediate 3-c and 40 ml of dichloromethane was added 1.93 ml of a 25% solution of ammonium hydroxide in 20 ml of water. After stirring for 10 min. at room temperature, the organic layer was separated, dried and filtered. Then there were added 7.15 ml of 2-propanol saturated with hydrochloric acid (3.5N). The whole was stirred for 1 hour and the product was filtered off and dried in vacuo at 45° C., yielding 6.8 g (84%) of (+)-6-[(4-chlorophenyl)hydrazinomethyl]-1-methyl-1H-benzotriazole monohydrochloride (interm. 4-d); enantiomeric excess: 98.6% g) 3.5 g of intermediate 4-d and 9.7 g of formamide was stirred for 3 hours at 145° C. Then there were added 22 ml of water and 22 ml of dichloromethane. The organic layer was separated, dried and evaporated. The residue was brought in 36 ml of 2-propanol and the obtained precipitate was filtered off. The mother liquor was evaporated and the residue was crystalized from 10 ml of 2-propanol, yielding 1.55 g (43%) of (+)-6-[(4-chlorophenyl)-(1H-1,2,4-triazol-1-yl)methyl]-1-methyl-1H-benzotriazole (comp. 1-b); enantiomeric excess: 96.4%.

Example 3 a) A mixture of 27.17 g of (4-chlorophenyl) (1-methyl-1H-benzotriazole-6-yl)methanone, 14.24 g of 1,1-dimethylethyl hydrazinecarboxylate and 80 ml of ethanol was stirred for 21 hours at reflux temperature. The reaction mixture was cooled to room temperature and stirring was continued for 2 hours. The precipitate was filtered off, washed with ethanol and dried in vacuo at 50° C., yielding 22.8 g (59.2%) of 1,1-dimethylethyl[(4-chlorophenyl)(1-methyl-1H-benzotriazol-6-yl)-methylene]hydrazine carboxylate (interm. 1-b).

b) To a suspension of 10 g of intermediate 1-b in 60 ml of tetrahydrofuran under a nitrogen atmosphere were added dropwise over 15 minutes 26 ml of a borane tetrahydrofuran complex in tetrahydrofuran (1M). After stirring for 15 minutes at ±22° C. there were added 13 ml of hydrochloric acid (6N). The whole was heated to reflux and refluxed for 1.5 hours. The mixture was cooled to room temperature and 50 ml of water were added. After stirring for 1 hour, the reaction mixture was filtered. The filtrate was mixed with 75 ml of methylbenzene. The layers were separated and the aqueous layer was basified (pH 7.5-8) with NH$_4$OH. The product was extracted with dichloromethane and the extract was dried, filtered and evaporated. The residue was converted into the hydrochloride salt in 2-propanol by adding 3 ml of a mixture of hydrochloric acid in 2-propanol (4.8N). After stirring for 2 hours the product was filtered off, washed with 2-propanol and dried in vacuo at 50° C., yielding 2.1 g of (±)-6-[(4-chlorophenyl)hydrazinomethyl]-1-methyl-1H-benzotriazole monohydrochloride (interm. 2-e).

Example 4

To a suspension of 27.2 g (4-chlorophenyl) (1-methyl-1H-benzotriazole-6-yl)-methanone in 100 ml of ethanol were added 7.77 g of hydrazide acetic acid. The whole was stirred for 44 hours at reflux temperature. After cooling, the product was filtered off, washed with ethanol and dried in vacuo at 45° C., yielding 13.6 g (41.5%) of [(4-chlorophenyl)(1-methyl-1H-benzotriazol-6-yl)methylene] hydrazide acetic acid (interm. 1-c).

Example 5

A mixture of 12.5 g of 6-[bromo(4-chlorophenyl)methyl]-1-methyl-1H-benzotriazole monohydrobromide, 70 ml of methylbenzene, 5.94 g of 1,1-dimethylethyl hydrazinecarboxylate and 11.5 ml of N-ethyl-N-(1-methylethyl)2-propanamine was stirred for 24 hours at 60° C. under a nitrogen atmosphere. The precipitate was filtered off at 50° C. and the flitrate was washed twice with water. The extract was acidified with 20 ml of hydrochloric acid (3N). After stirring for 5 hours at 60° C., the whole was cooled and the layers were separated. The aqueous layer was washed with dichloromethane. The aqueous layer was basified with NH$_4$OH and extracted with dichloromethane. The dried extract was evaporated and the residue was converted into the hydrochloride salt in 2-propanol. After stirring for 1 hour at 22° C. and 2 hours at 5° C. (ice-bath) the salt was filtered off and dried in vacuo at 45° C. during 20 hours, yielding 2.5 g (25.7%) of (±)-6-[(4-chlorophenyl)hydrazinomethyl]-1-methyl-1H-benzotriazole monohydrochloride (interm. 2-f).

Example 6

A mixture of 7.5 g of intermediate 3-a and 17 ml of methanol was heated to reflux temperature. The precipitate was filtered off. The filtrate was mixed with 5.3 g of methanimidamide monoacetate and stirred for 2.5 hours at reflux temperature. At 66° C. there were added 8.5 ml of water. The product crystallized and the reaction mixture was cooled slowly. The whole was stirred for 1 hour at room temperature. Then there were added 4.3 ml of water and stirring was continued for 1 hour at room temperature. The precipitated was filtered off and dried at 50° C., yielding 4.2 g of impure product. A mixture of 4.2 g of the product, 12.6 ml of 2-propanol and 0.21 g activated charcoal was refluxed for 15 minutes. The charcoal was filtered off while hot. The filtrate was cooled and the formed precipitate was filtered off, washed with 2 ml of 2-propanol and dried in vacuo at 50° C., yielding 3.0 g (54%) of (+)-6-[(4-chlorophenyl)-(1H-1,2,4-triazol-1-yl)methyl]-1-methyl-1H-benzotriazole (comp. 1-c); enantiomeric excess: 99%.

Example 7

To a mixture of 3.1 g of intermediate 2-d and 30 ml dichloromethane was added a solution of 0.4 g of sodium hydroxide in 30 ml of water. After stirring for 15 minutes at 22° C., the organic layer was separated, dried, filtered and evaporated. The residue was taken up in 2-propanol and there were added 2.7 g of 4-(2-chloro-phenyl)-dihydro-2-hydroxy-5,5-dimethyl-4H-1,3,2-dioxaphosphorin-2-oxide. After stirring at 22° C., the precipitate was filtered off, washed with 2-propanol and dried at 50° C., yielding 2.6 g (92%) of 6-[(4-chlorophenyl)hydrazinomethyl]-1-methyl-1H-benzotriazole 4-(2-chlorophenyl)-dihydro-2-hydroxy-5,5-dimethyl-4H-1,3,2-dioxaphosphorin-2-oxide (interm. 5-a); diastereomeric excess: 24.8%.

Example 8

A mixture of 67 g of intermediate 2-d, 300 ml of water, 10 ml NaOH aq. (50%) and 300 ml of dichloromethane was stirred for 15 minutes at 22° C. The organic layer was separated, washed with water, dried, filtered and evaporated. The residue was converted into the (S)-(−)-α-[[(phenylamino)carbonyl]oxy]propanoate salt in 500 ml of 2-propanol. After stirring for 16 hours at 40° C., the precipitate was filtered off and washed with 25 ml of 2-propanol. The product was dried at 50° C., yielding 46 g (92%) of (−)-6-[(4-chlorophenyl)hydrazinomethyl]-1-methyl-1H-benzotriazole (S)-α-[[(phenylamino)carbonyl]oxy]propanoate (interm. 6-a). $[\alpha]_D^{20}=7.65°$ (conc.=1% in DMF); diastereomeric excess: 40%.

b) A mixture of 20 g of intermediate 6-a, 60 ml of dichloromethane, 50 ml of water and 2.1 ml NaOH aq. (50%) was stirred for 10 minutes at 20° C. The organic layer was separated, washed with water, dried and filtered. Then there was added a solution of 6.7 ml of HCl in 2-propanol (6N) and the whole was evaporated. The residue was taken up in 150 ml of ethanol and there were added 3.3 g of 1,3,5-triazine. After stirring for 50 minutes at reflux temperature, the reaction mixture was evaporated and the residue was taken up in a mixture of 60 ml of water and 80 ml of dichloromethane. The whole was basified with NH$_4$OH aq. and stirred for 5 minutes at 20° C. The organic layer was separated, washed with water, dried, filtered and evaporated, yielding an oily residue of (−)-6-[(4-chlorophenyl)(1H-1,2,4-triazol-1-yl)methyl]-1-methyl-1H-benzotriazole (comp 1-d).

Example 9 a) A mixture of 10 g of intermediate 4-a, 100 ml of ethyl formate and 4.5 ml of N,N-diethylethanamine was stirred for 20 hours at reflux temperature. After cooling, the reaction mixture was poured into 300 ml of water. The product was extracted with dichloromethane and the extract was dried, filtered and evaporated. The residue was crystallized in 2-propanol and dried in vacuo, yielding 6.2 g (63.7%) of 2-[(4-chlorophenyl)(1-methyl-1H-benzotriazol-6-yl)methyl]hydrazinecarboxaldehyde (interm. 7-a).

b) A mixture of 5 g of intermediate 7-a, 8.2 g of methanimidamide monoacetate in 32 ml of methanol was refluxed for 3 days. To the warm reaction mixture there were added 32 ml of water and the resulting mixture was stirred for two hours. The precipitate was filtered off and washed with 2-propanol. The precipitate was dried in vacuo, yielding 3.45 g (67%) of (+)-6-[(4-chlorophenyl)-(1H-1,2,4-triazol-1-yl)methyl]-1-methyl-1H-benzotriazole (comp. 1-e); enantiomeric excess: 97.4%.

Example 10 a) To a mixture of 142 g of intermediate 2-d and 340 ml of ethanol under a nitrogen atmosphere was added a solution of 17 g of sodium hydroxide in 127.8 ml of water. The whole was stirred for 10 minutes at 23° C. At 40° C. were added 42.55 g of (R)-(−)-α-hydroxybenzeneacetic acid and stirring was continued at 70°-75° C. After cooling spontaneously, the product was filtered off, washed with ethanol and dried at 50° C., yielding 88.5 g (87.5%) of (−)-6-[(4-chlorophenyl)hydrazinomethyl]-1-methyl-1H-benzotriazole (R)-α-hydroxybenzeneacetate (1:1) monohydrate (interm. 3-d).

b) The mother liquor was acidified with hydrochloric acid and the whole was evaporated up to ⅕ of the volume. Then there were added 100 ml of water and 400 ml of dichloromethane. The whole was basified with sodium hydroxide (50%). The organic layer was dried, filtered and evaporated. The product was converted into the hydrochloride salt in 2-propanol by adding a mixture of hydrochloric acid and 2-propanol (3N). The salt was filtered off, washed with dichloromethane and dried at 50° C., yielding 57.7 g (41.8%) of (−)-6-[(4-chlorophenyl)hydrazinomethyl]-1- methyl-1H-benzotriazole monohydrochloride (interm. 8-a); enantiomeric excess: 82.8%.

c) A mixture of 10 g of intermediate 4-a, 1.25 g of sodium hydroxide, 31 ml of water and 90 ml of dichloromethane was stirred for 15 minutes at 25° C. The organic layer was separated, dried, filtered and evaporated. Then, there were added 20 ml of methylbenzene and the whole was evaporated again. The residue was taken up in 20 ml of dichloromethane and there were added 3.17 g of acetic acid art hydride. After stirring for 5 hours at 40° C. and overnight at room temperature there were added 35 ml of water. The whole was basified with NaOH 50%. After stirring for 5 minutes, the organic layer was separated, dried, filtered and evaporated. The product was recrystallized from ethanol, yielding 6.10 g (60%) of (+)-[(4-chlorophenyl)-(1-methyl-1H-benzotriazol-6-yl)methyl]hydrazide acetic acid (interm. 9-a); enantiomeric excess: 97.2%

Example 11 a) To a solution of 64.2 g of 6-[chloro(4-chlorophenyl)methyl]-1-methyl-1H-benzotriazole in 600 ml of acetonitrile were added dropwise 300 ml of hydrazine hydrate. After stirring for 30 hours at reflux temperature, the reaction mixture was poured into a mixture of ice water and potassium carbonate (aq.). The product was extracted with 1,1'-oxybisethane and the extract was washed with water, dried, filtered and evaporated. The oily residue was crystallized from 1,1'-oxybisethane, yielding 42 g (66.4%) of (±)-6-[(4-chlorophenyl)hydrazinomethyl]-1-methyl-1H-benzotriazole (interm. 10-a); mp. 96° C.

b) To a solution of 9.2 g of intermediate 10-a in 90 ml of tetrahydrofuran at room temperature under a nitrogen atmosphere were added successively 5.3 g (R)(-)-methoxybenzene acetic acid and 4.3 g of 1-hydroxybenzotdazole. Then there was added dropwise a solution of 6.6 g of N,N'-dicyclohexylcarbodiimide in 60 ml of dichloromethane and the whole was stirred for 2 hours at room temperature. The reaction mixture was evaporated and the residue was taken up in dichloromethane. The reaction mixture was filtered and the filtrate was washed with $K_2CO_3$ (aq. 10%). The organic layer was separated, dried, filtered and evaporated. The residue was purified by column chromatography (HPLC: silica gel; cyclohexane/2-propanol 70:30), yielding 2 diastereomerically pure fractions. The fluent of the desired fractions was evaporated and the residue was dried, yielding 4.5 g (32.3%) and 3.9 g (28.0%) of (A) and (B) (R)-α-methoxybenzeneacetic acid, $N^2$-[(4-chlorophenyl)(1-methyl-1H-benzotriazol-6-yl)methyl] hydrazide (interm. 11-a and 11-b). c) A mixture of 4.5 g of 11-a, 45 ml of hydrochloric acid (6N) and 20 ml of ethanol was stirred for 2 hours at reflux temperature. The mixture was basified with $NH_4OH$ and the product was extracted with ethyl acetate. The extract was dried, filtered and evaporated, yielding enantiomerically pure (A)-6-[(4-chlorophenyl)hydrazinomethyl]-1-methyl-1H-benzotriazole (interm. 12-a).

d) A mixture of 3.9 g of intermediate 11-b, 40 ml of hydrochloric acid (6N) and 20 ml of ethanol was stirred for 2 hours at reflux temperature. The mixture was basified with $NH_4OH$ and the product was extracted with ethyl acetate. The extract was dried, filtered and evaporated, yielding enantiomerically pure (B)-6-[(4-chlorophenyl)hydrazinomethyl]-1-methyl-1H-benzotriazole (interm. 12-b).

We claim:
1. A process for preparing enantiomerically pure 6-[(4-chlorophenyl) (1H-1,2,4-triazol-1-yl)methyl]-1-methyl-1H-benzotriazole having the formula:

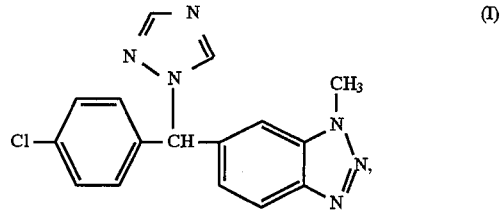

or a pharmaceutically acceptable acid addition salt form thereof, which comprises the steps of (a) resolving the racemic mixture of an intermediate of the formula:

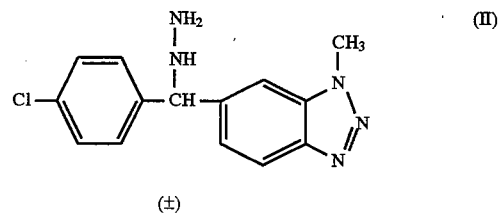

by adding said racemic mixture of the intermediate of Formula (II) to a chiral acid, thereby forming a mixture of diastereomeric salts with one of the enantiomers of a chiral acid, (b) crystallizing said mixture, (c) thereafter collecting the desired diastereomeric salt of Formula (A)(III) either from the precipitate or from the mother liquor:

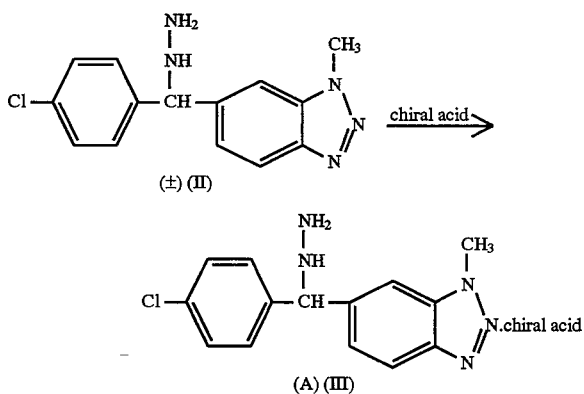

and (d) converting the salt of Formula (A)(III) into an enantiomerically pure form of the compound of Formula (I) by cyclization with methanimidamide, triazine, formamide or an acid addition salt thereof,
wherein the chiral acid is selected from the group consisting of (R)-(-)-α-hydroxybenzeneacetic acid; (+)-4-(2-chlorophenyl)-dihydro-2-hydroxy-5,5-dimethyl-4H-1,3,2-dioxaphosphorin-2-oxide; and (S)-(-)-α-[[(phenylamino)carbonyl]oxy]propanoic acid.

2. The process of claim 1 wherein the chiral acid salt product of step (d) is converted into the free base form by treatment with an alkali.

3. The process of claim 1 wherein the chiral acid is (R)-(-)-α-hydroxybenzeneacetic acid.

4. The process of claim 2 wherein the chiral acid is (R)-(-)-α-hydroxybenzeneacetic acid.

* * * * *